United States Patent [19]
Reilly et al.

[11] Patent Number: 5,955,080
[45] Date of Patent: Sep. 21, 1999

[54] SELF-ADJUVANTING PEPTIDE VACCINE DELIVERY SYSTEM AND PRODUCTION THEREOF

[75] Inventors: Wayne Gerard Reilly, Northmead; Robert George Whittaker, West Pymble; Phillp Anthony Jennings, North Ryde; Kenneth Geoffrey Finney, Ryde, all of Australia

[73] Assignee: Commonwealth Scientific and Industrial Research Organisation, Campbell, Australia

[21] Appl. No.: 08/871,689

[22] Filed: Jun. 9, 1997

Related U.S. Application Data

[63] Continuation of application No. 08/185,878, filed as application No. PCT/AU92/00377, Jul. 24, 1992, abandoned.

[30] Foreign Application Priority Data

Jul. 26, 1991 [AU] Australia ................................ PK7457

[51] Int. Cl.$^6$ ........................ A61K 39/385; A61K 45/00; A61K 39/02; A61K 39/00
[52] U.S. Cl. .................................... 424/194.1; 424/184.1; 424/185.1; 424/195.1; 424/197.1; 424/242.1; 424/278.1
[58] Field of Search .............................. 424/184.1, 185.1, 424/195.1, 194.1, 197.1, 242.1, 278.1

[56] References Cited

U.S. PATENT DOCUMENTS

| | | | |
|---|---|---|---|
| 4,608,251 | 8/1986 | Mia | 424/85 |
| 4,717,716 | 1/1988 | Nagai et al. | 514/19 |
| 5,017,558 | 5/1991 | Vyas . | |
| 5,100,664 | 3/1992 | Doyle et al. | 424/92 |

FOREIGN PATENT DOCUMENTS

| | | |
|---|---|---|
| A-22755/88 | 9/1987 | Australia . |
| 0 069 659 | 1/1983 | European Pat. Off. . |
| 0 203 676 | 12/1986 | European Pat. Off. . |
| 0 578 293A1 | 1/1994 | European Pat. Off. . |
| 40 03 944 | 8/1991 | Germany . |
| 2 170 707 | 8/1986 | United Kingdom . |
| WO88/00056 | 1/1988 | WIPO . |
| WO 88/01176 | 2/1988 | WIPO . |
| WO 88/053308 | 7/1988 | WIPO . |
| WO 88/08430 | 11/1988 | WIPO . |
| WO 89/10348 | 11/1989 | WIPO . |
| WO 90/03182 | 4/1990 | WIPO . |
| WO91/09837 | 7/1991 | WIPO . |

OTHER PUBLICATIONS

Wiesmüller et al. 1989 Vaccine 7:29–33.
Smith et al. Tech. Adv. in Vacc. Dev. 1988 pp. 651–659.
Lowell et al. 1988 Science 240:800–802.
Lowell et al 1988 Tech. Adv. in Vacc. Dev. pp. 423–432.
Ladd et al, Am J Reprod Immunol 22(1–2): 56–63, 1990.
Sherwood et al, Proc. Natl. Acad. Sci. USA 80: 2794–2798, 1983.
Lovejoy et al, Regul. Pept. 33: 105–116, 1991.
Geysen et al, J. Molecular Recognition 1(1):32–42, 1988.
Kumar et al, Proc. Natl. Acad. Sci. USA 87: 1337–1341, 1990.
Jennings et al, Protein Engineering 2(5):365–369, 1989.
Harlow et al, Antibodies: A Laboratory Manual, Cold Spring Harbor Laboatory, 1988, pp. 124, 127–129.
Murray et al, Harpers Biochemistry, 21st Ed., Appleton and Lange, Norwalk CT, 1988, p. 37.
Pearce et al Microbiology 140/1:205–211 1994.

*Primary Examiner*—Nita Minnifield
*Attorney, Agent, or Firm*—McDermott, Will & Emery

[57] ABSTRACT

The present invention provides self-adjuvanting vaccines for use in raising antibodies to peptides without the use of oil or alum adjuvants. Further, the present invention provides methods of therapy using these vaccines and has particular application in chemical castration. In one aspect the vaccine comprises in admixture a peptide conjugated to 1–3 fatty acids and a peptide conjugated to a carrier protein. In preferred forms the peptide is conjugated to the fatty acids via a tromethamine or ethanolamine derivative. The preferred protein carrier is Type 4 fimbriae.

11 Claims, 17 Drawing Sheets

5,955,080

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:1:

Ser Gly Gly Trp Ser Tyr Gly Leu Arg Pro Gly Gly
    1               5                    10

(2) INFORMATION FOR SEQ ID NO:2:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:2:

Trp Ser Tyr Gly Leu Arg Pro

```
(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:3:

Trp Ser Tyr Gly Trp Leu Pro
   1               5

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:4:

Trp Ser Tyr Gly Leu Gln Pro
   1               5
```

SELF-ADJUVANTING PEPTIDE VACCINE DELIVERY SYSTEM AND PRODUCTION THEREOF

This application is a continuation of application Ser. No. 08/185,878 filed May 3, 1994 now abandoned.

BACKGROUND OF THE INVENTION

The present invention relates generally to self-adjuvanting vaccines for use in raising antibodies to peptides without the use of oil or alum adjuvants. The present invention further relates to the use of this vaccine and to methods of therapy. The present invention has particular application in chemical castration.

The use of leutinising hormone releasing hormone (LHRH) in chemical sterilisation of both male and female immunized with preparations including LHRH and this immunisation leads to dysfunction of the gonads and consequent induced sterility. In male animals reduction in testicular size relative to untreated controls may be clearly seen. Unfortunately, the mere immunisation with LHRH is not a totally effective method of chemical castration. Typically, whilst in the majority of one group of animals the immunisation with LHRH will have the desired effect, the immunisation will have little effect on a number of animals in that sample. As will be readily appreciated this is a significant drawback because, for example, if one unaffected male remains in the immunised herd this male may fertilise a number of females within the herd. For this reason chemical sterilisation utilising LHRH has to date achieved only limited application, with physical and other methods of sterilisation still predominating.

In the present applicant's copending Austrailian patent application No 17049/88 there is disclosed an effective method of peptide production by protein engineering. This method involves the culturing of genetically engineered bacteria which produce, as extracellular structures, Type 4 fimbriae, the peptide being produced in association with these fimbriae. This method comprises culturing bacteria containing the gene encoding the fimbrial subunit of Type 4 fimbriae to which has been added at the C-terminal end the nucleic acid sequence encoding the desired peptide. In further work on this system the present inventors have found that not only does this method provide a simple and efficient means of producing a peptide but that the fimbrial protein acts as a powerful immunoadjuvant.

The present inventors have also produced a peptide having a sequence derived from LHRH in association with Type 4 fimbriae. It has been found that this peptide conjugated to bacterial Type 4 fimbriae provides a very effective chemical sterilisation agent.

In the present applicant's copending International Patent Application No PCT/AU90/00599 (the disclosure of which is incorporated herein by reference) there is disclosure of means of linking fatty acids and the like to peptides.

The present inventors have also found that co-administration of a peptide/fatty acid conjugate with a peptide/carrier protein (such as fimbrial protein) conjugate yields a heightened antibody response to the peptide.

In addition the present inventors have found that the antibody response in an animal can be enhanced by the use of the fimbrial protein of a Type 4 fimbriate bacteria.

SUMMARY OF THE INVENTION

Accordingly, in a first aspect the present invention consists in a vaccine for use in raising an immune response to a peptide, the vaccine comprising in admixture the peptide conjugated to 1 to 3 fatty acids and the peptide conjugated to a carrier protein.

In a preferred embodiment of the first aspect of the present invention the peptide has or includes one of the following amino acid sequences:

SGGWSYGLRPGG; (SEQ ID NO:1)
WSYGLRP; (SEQ ID NO:2)
WSYGWLP; or (SEQ ID NO:3)
WSYGLQP. (SEQ ID NO:4)

In a second aspect the present invention consists in a vaccine for use in chemical sterilisation the vaccine comprising a peptide which has or includes an amino acid sequence selected from the group consisting of:

SGGWSYGLRPGG (SEQ ID NO:1), WSYGLRP (SEQ ID NO:2), WSYGWLP (SEQ ID NO:3) and WSYLLQP (SEQ ID NO:4), the peptide being conjugated either to 1 to 3 fatty acids or to a fimbrial subunit.

In a preferred embodiment of the invention the carrier protein is a fimbrial sub unit protein, ovalbumin, bovine serum albumin, tetanus toxin, or keyhole limpet haemocyanin. It is presently preferred, however, that the carrier protein is a fimbrial protein subunit and that the subunit proteins are assembled into fimbriae. It is most preferred that the fimbriae are Type 4 fimbriae.

The peptide is preferably conjugated to 1 to 3 fatty acids via a tromethamine or an ethanolamine derivative.

It is presently preferred that the peptide is linked to three fatty acids and more preferably that each are the same fatty acid. It is also preferred that the fatty acid has a carbon chain of 3 to 18 carbon atoms and most preferably 16 carbon atoms.

The present inventors have also found that partial denaturation of the peptide/fimbrial protein carrier results in a higher antigenic response. This partial denaturation is preferably obtained by treatment of the peptide/carrier protein at a pH of less than or equal to 4 and preferably at a pH of about 1. Given the enhanced response that this partial denaturation provides in a preferred form of the invention the peptide/fimbrial protein conjugate is subjected to a a partial denaturation prior to admixture with the peptide/fatty acid conjugate.

As will be appreciated by those skilled in the art while any peptide can be used in the vaccine of the first aspect of the present invention the preferred peptides are LHRH derived peptides. Where the peptide is an LHRH peptide, or a derivative, the vaccine may be used for chemical sterilization of animals or for use as an alternative to the present LHRH agonist and antagonist therapy for human sex hormone dependent cancers. Four of the most commonly occurring human sex hormone dependent cancers are prostate, breast, endometrial and ovarian cancer. These conditions may be susceptible to treatment by vaccination with the vaccine of the present invention using the LHRH peptide or derivative. The vaccine of the present invention could also be used as an adjunct to the present LHRH agonist and antagonist therapy for these diseases.

It will be appreciated by those skilled in the art that a number of modifications may be made to the peptides preferably used in the present invention without deleteriously effecting the biological activity of the peptide. This may be achieved by various changes, such as insertions, deletions and substitutions, either conservative or non-conservative in the peptide sequence where such changes do not substantially alter the nature of the immune response raised by the peptide. By conservative substitutions the intended combinations are:

G,A; V,I,L,M; D,E; N,Q; S,T; K,R,H; and F,Y,W.

The vaccine of the first aspect of the present invention will also have applicability in the treatment of diseases such as AIDS, malaria, influenza, zone pellucida peptide epitopes or hepatitis where peptide epitopes have been identified and a vaccine approach is possible.

The vaccine of the first aspect of the present invention comprising an admixture of peptide/fatty acid conjugate with peptide/carrier protein conjugate when used without oil or alum adjuvants induces high level antibody responses in animals. The ability of this vaccine to induce such high level response without requiring oil or alum based adjuvants is of particular benefit. Such findings will allow the use of this vaccine where the use of oil based adjuvants is not permitted and the use of alum based adjuvants is being questioned, e.g., human vaccines or vaccines for companion animals.

The preferred form of preparing the peptide/type 4 fimbrial protein conjugate involves using the method disclosed in Australian patent application No 17049/88. By using this method the desired peptide can be expressed in association with Type 4 fimbriae by genetically engineered strains of Pseudomonas. This method is, however, to some extent, limited in that the peptide epitope size that can be incorporated into the fimbriae is dependent on the degree of modification which can be made before the fimbriae is no longer properly assembled. Investigations have shown that peptides of up to approximately 20 amino acid residues can be produced in association with the fimbriae in *Pseudomonas aeruginosa*. Accordingly, it is presently preferred that the peptides are able to be expressed in association with fimbriae in *Pseudomonas aeruginosa*. If, however, the peptide epitope is too large or cannot be expressed in this fimbrial system it is still possible to use the vaccine of the present invention by simply chemically conjugating the peptide with the fimbrial protein.

The response to the vaccine component of the present invention may also be enhanced by the use of T-cell, $H_2$ receptor antagonists, e.g., cimetidine or carnosine, or other immunomodulators e.g., cytokines or immunostimulatory peptides which may act as immunomodulators to overcome carrier protein unresponsiveness or to further enhance the immune system.

The present inventors also believe that the antibody response in an animal to an antigen may be heightened by the use of fimbrial protein of a Type 4 fimbriate bacteria.

Accordingly, in a third aspect the present invention consists in a method of enhancing the antibody response to an antigen in an animal, the method comprising to the animal an effective amount of the antigen conjugated to the fimbrial protein of a Type 4 fimbriate bacteria.

As is disclosed in application No PCT/AU90/00599 a wide range of fatty acids may be linked to the peptide via a tromethamine or ethanolamine derivative. In addition, 1–3 fatty acids may be linked to the peptide. It should also be noted that the peptide linked to the fatty acids can be of virtually unlimited size.

In order that the nature of the present invention may be more clearly understood a preferred form thereof will now be described with reference to the following examples and figures in which:

FIGS. 1–4 show the results of a comparative vaccination trial using ten animals/group, mice were given two vaccinations at four week intervals and data collected four weeks after the second vaccination; (FIG. 1 control, FIG. 2 100 µg untreated LHRH-fimbriae and Freund's Incomplete Adjuvant (FIA), FIG. 3 Wild Type Fimbriae, FIG. 4 untreated LHRH-Fimbriae admixture with LHRH ala-tris-tripalmitate (ATP3) conjugate;

FIG. 5 shows the antibody response for the animals set out in FIGS. 2 and 4, the light hatch represents the serum LHRH antibody levels for group in FIG. 2 and the dark hatch group FIG. 4. Groups FIG. 1 and FIG. 3 had not LHRH antibodies;

FIGS. 6(a)–(d) show the results of admixture vaccinations using LHRH-acid treated fimbriae or LHRH-ovalbumin conjugate with the ATP3 conjugate. Four groups of ten mice were given a primary vaccination followed by a secondary vaccination four weeks later.

FIG. 6(a) mice vaccinated with acid treated LHRH-fimbriae adjuvanted with FIA (ATF-FIA);

FIG. 6(b) mice vaccinated with acid treated LHRH-fimbriae in admixture with ATP3 conjugate (ATF-ATP3);

FIG. 6(c) mice vaccinated with LHRH-ovalbumin conjugate adjuvanted with FIA (OV-FIA); and FIG. 6(d) mice vaccinated with LHRH-ovalbumin conjugate in admixture with ATP3 conjugate (OV-ATP3). Testes weights are presented for each individual animal;

Figure 9A:
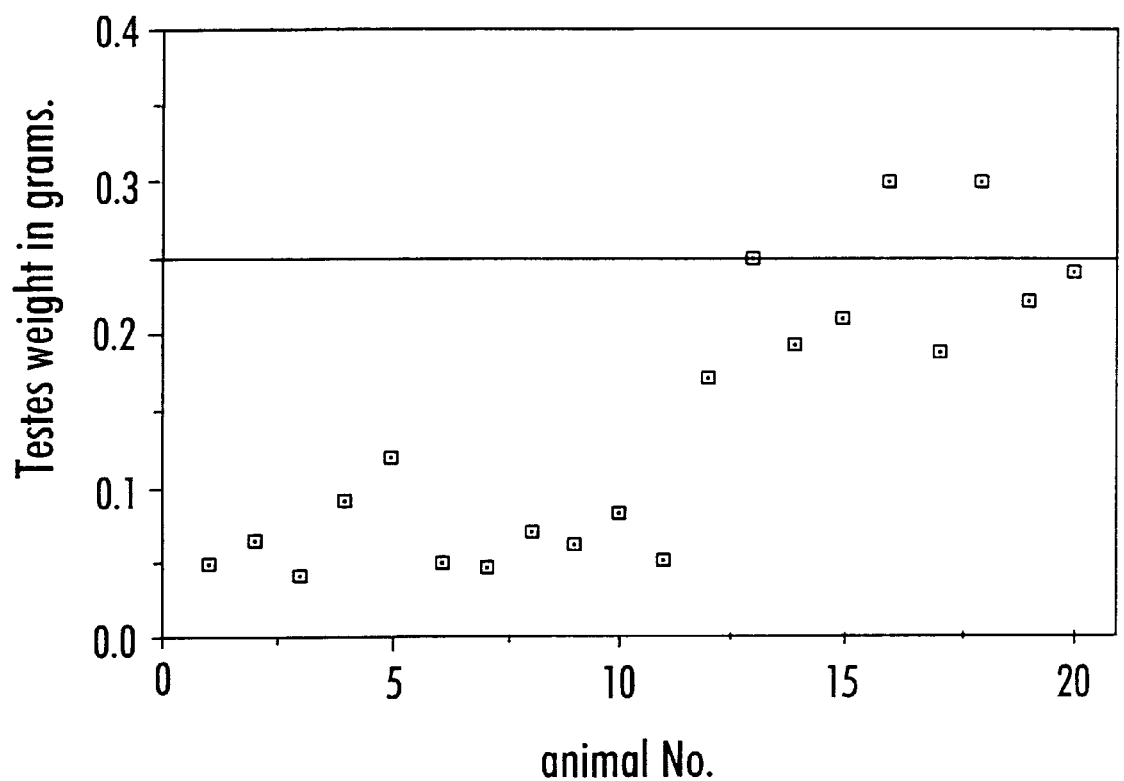
Figure 9B:
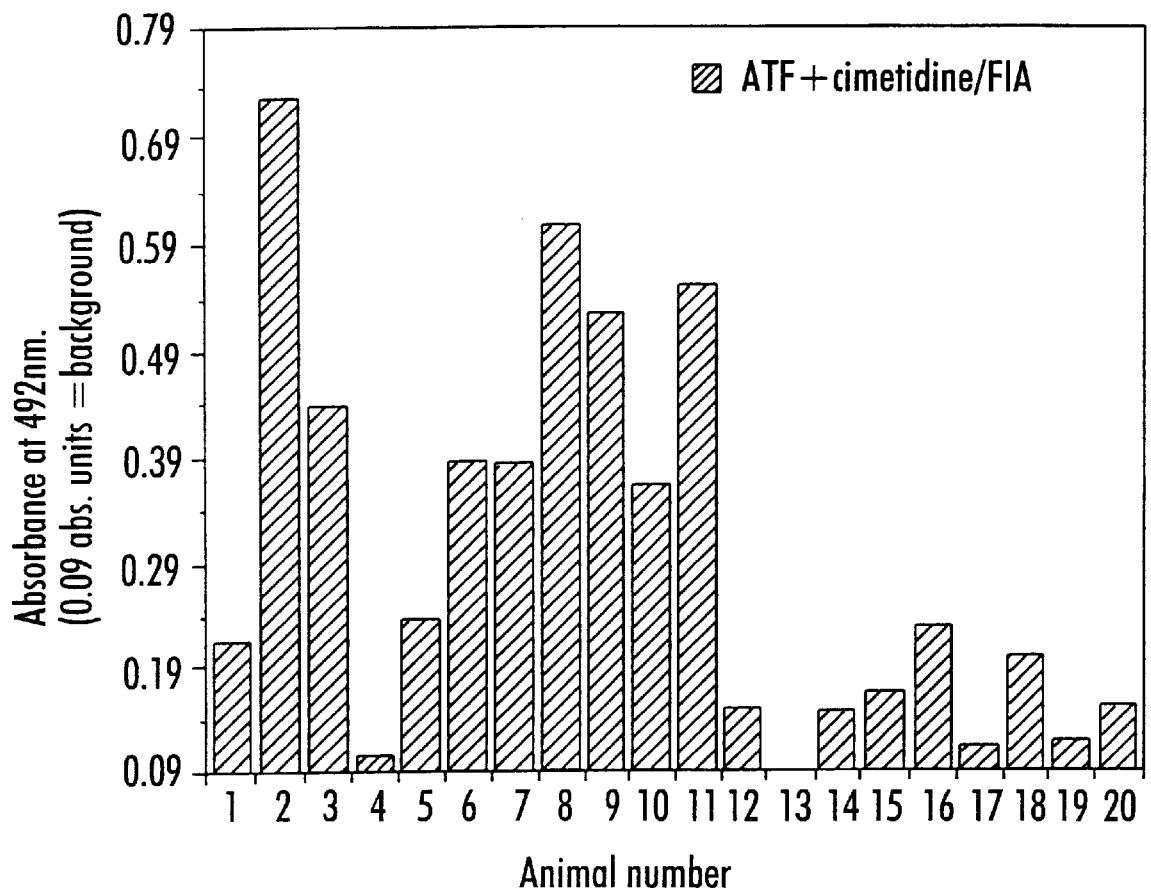
Figure 10A:
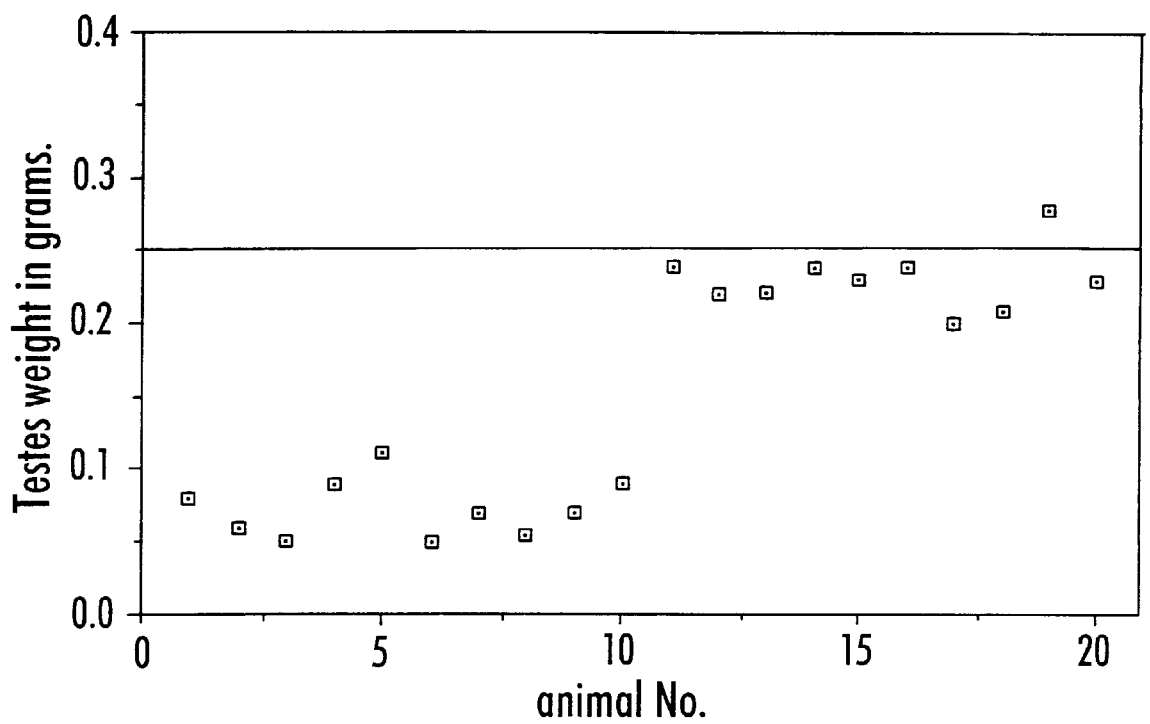
Figure 10B:
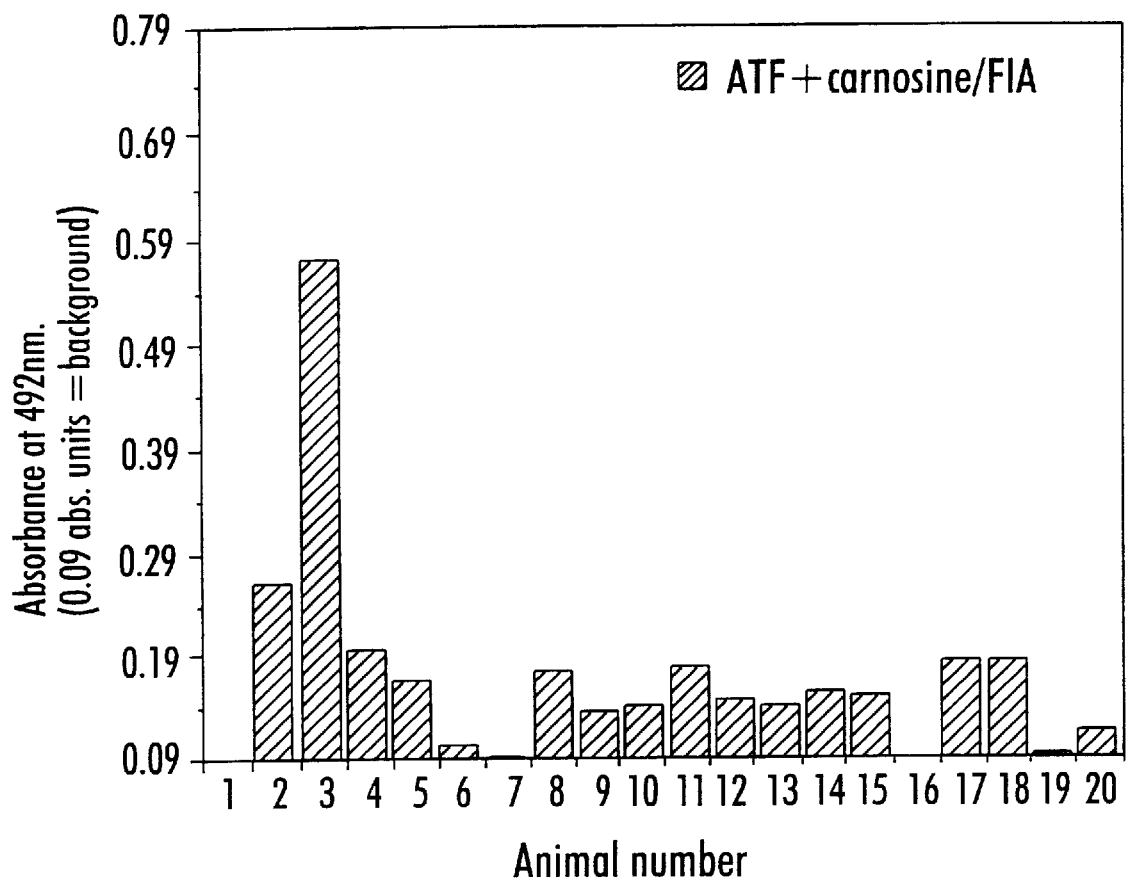
Figure 11A:
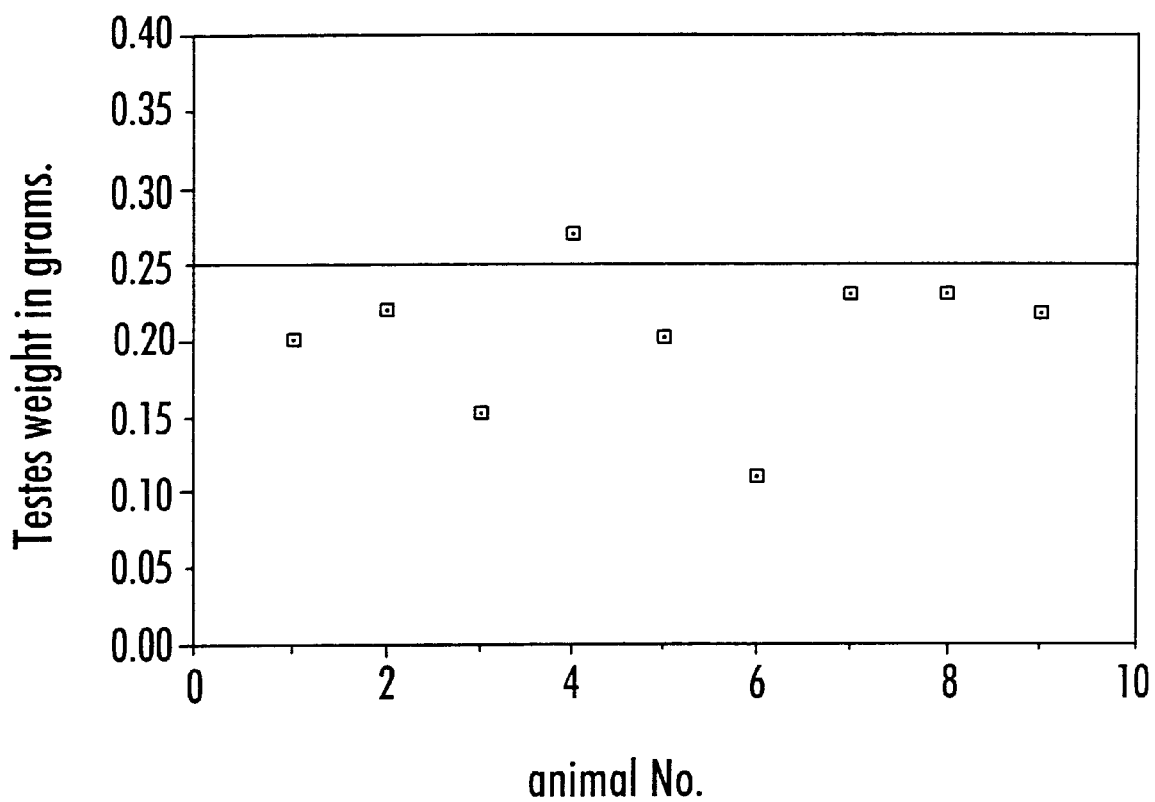
Figure 11B:
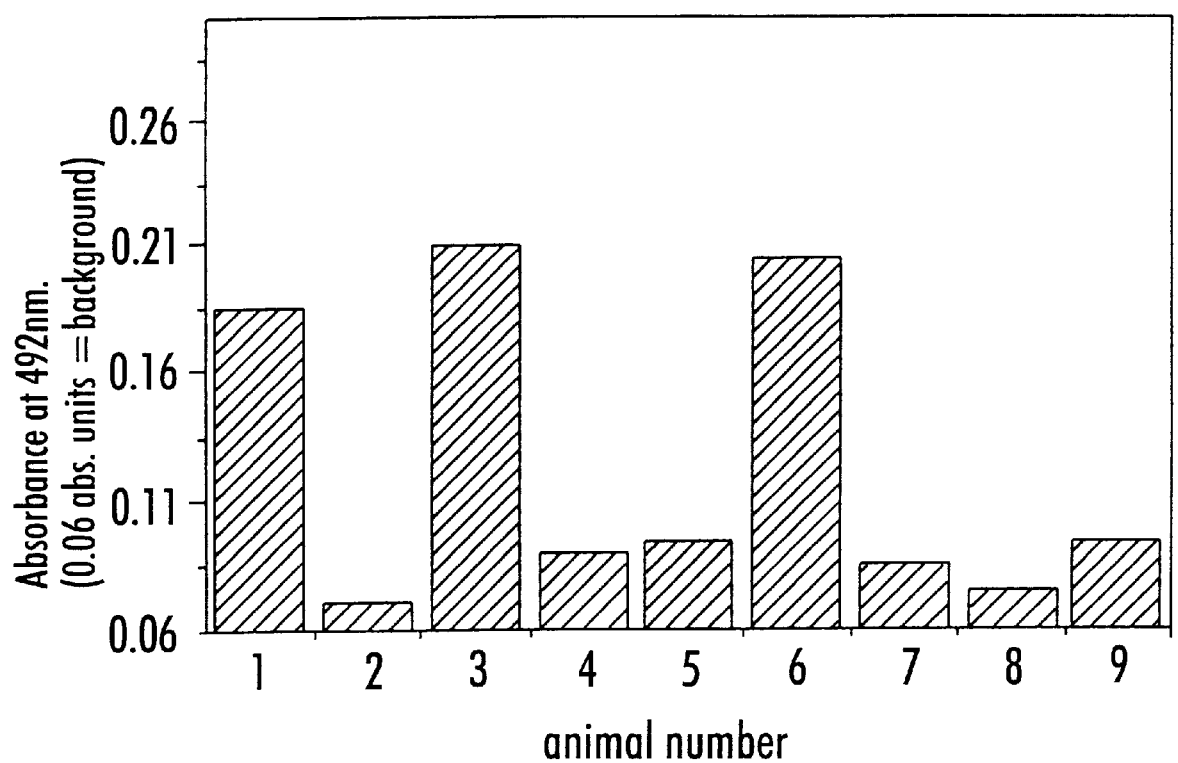
Figure 12A:
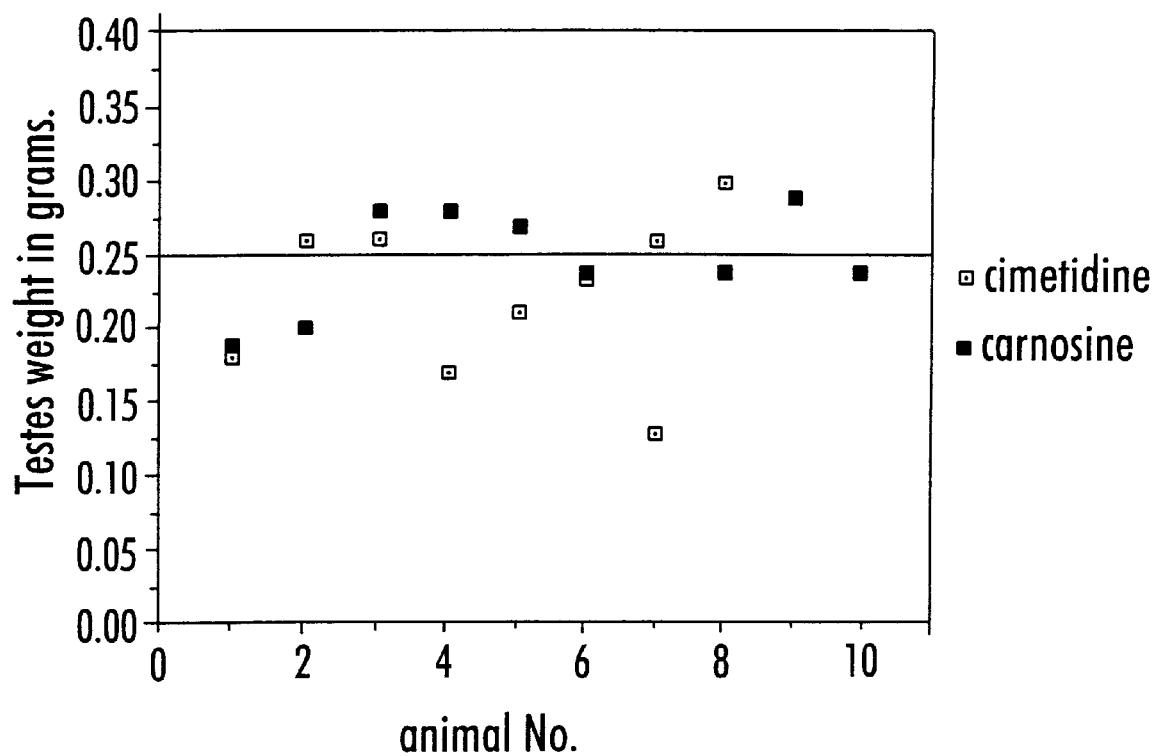
Figure 12B:
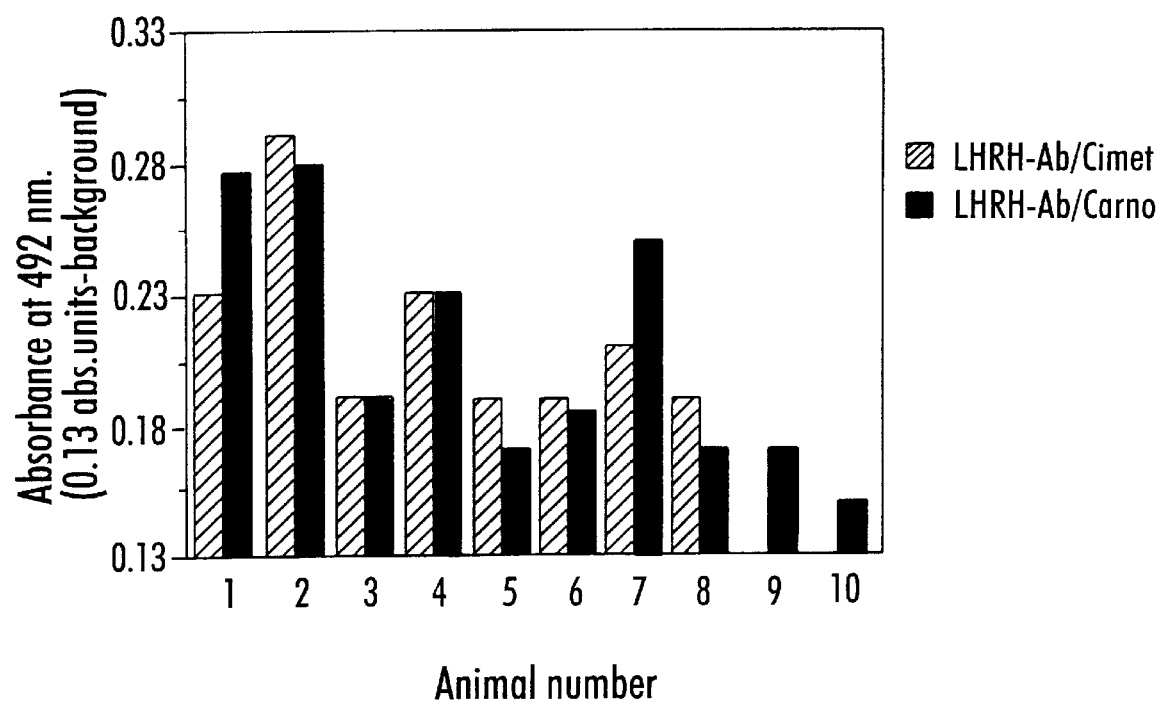

FIGS. 9(a)–(b) show the results of mouse vaccination trials using acid treated LHRH-fimbriae adjuvanted with FIA and potentiated with cimetidine (100 µl of 5 mg/ml given every second day for 6 days after vaccination). The mice were vaccinated with 100 µg of fimbrial protein given subcutaneously and revaccinated four weeks later. The testes weights and LHRH antibody levels for each individual mouse are shown in FIGS. 9a and 9b respectively;

FIGS. 10(a)–(b) show the results of mouse vaccination trials using acid treated LHRH-fimbriae, immunopotentiated with carnosine (100 µl of 5 mg/ml given every second day for 6 days after vaccination) and adjuvanted with FIA. The mice were vaccinated with 100 µg of fimbrial protein given subcutaneously and revaccinated four weeks later. The testes weights and LHRH antibody levels for each individual mouse are shown in FIGS. 10a and 10b respectively;

FIGS. 11(a)–(b) show the results of a mouse vaccination trial using acid treated LHRH-fimbriae in a water/glycerol mixture and not adjuvanted with oil or alum. The mice were vaccinated with 150 mg of protein subcutaneously and given a booster vaccination four weeks later. The testes weights and LHRH antibody levels for each individual mouse four weeks after the booster vaccination are shown in FIGS. 11a and 11b respectively; and FIGS. 12(a)–(b) show the results of mouse vaccination trials using acid treated LHRH-fimbriae in admixture with LHRH-ATP3 and immunopotentiated with either cimetidine or carnosine. The mice were given a primary vaccination with 100 mg acid treated LHRH-fimbriae together with 2 mg of LHRH-ATP3 and immunopotentiated with three doses of 500 mg of either cimetidine or carnosine. A secondary vaccination was given four weeks later, the testes weights and LHRH antibody levels for each individual mouse eight weeks after the primary vaccination is shown in FIGS. 12a (☐cimetidine, ■carnosine) and 12b (☐cimetidine, ■carnosine) respectively;

Materials and Methods

Plasmids and bacterial strains

The multifunctional vector pFEM2 was constructed and used for oligonucleotide-directed mutagenesis of the fimbrial subunit gene and for the testing of the fimbrial expression of modified subunits in *P. aeruginosa*. In brief, the plasmid contains a c1857 gene cartridge obtained from pC121 and a fimbrial subunit expression cartridge from pJSM129. These were recombined to give a vector which can replicate in *E. coli* and *P. aeruginosa*, has a M13 intergenic region for the production of single stranded DNA and carries a *Dichleobacter nodosus* A1 serotype fimbrial subunit expression cartridge. Regulated expression of the fimbrial subunit is possible because of the plasmid-borne c1857 gene. The *P. aeruginosa* strain K/2Pfs was used for fimbrial subunit expression. Competent cells were prepared using the procedure described for *P. aeruginosa*. Transformed cells were propagated at 37° C. or at 42° C. when fimbrial subunit expression was desired. *P. aeruginosa* transformants were cultured in Trypticase Soy Broth (TSB, 30 gms/liter) containing 0.15 mg/ml carbenicillin.

Expression of Fimbrial Subunit Bearing the LHRH Graft

Figure 1:
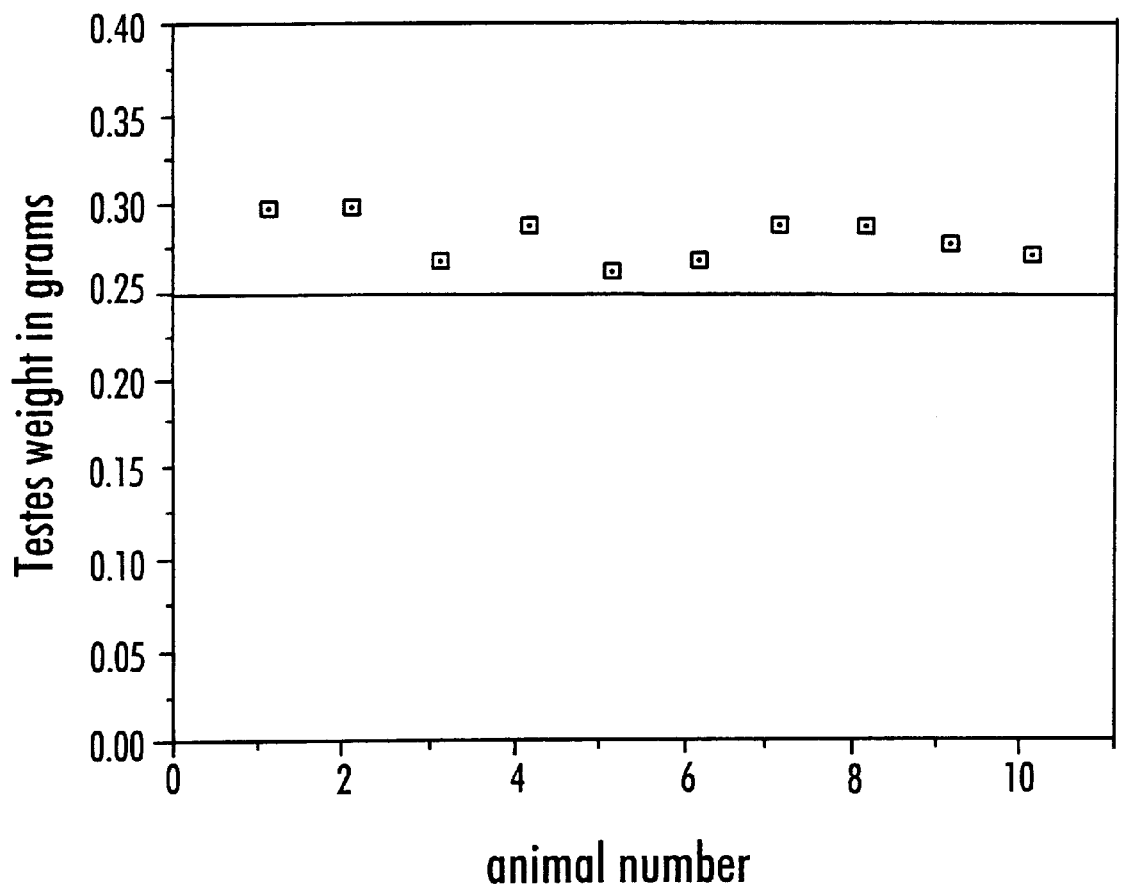
Figure 2:
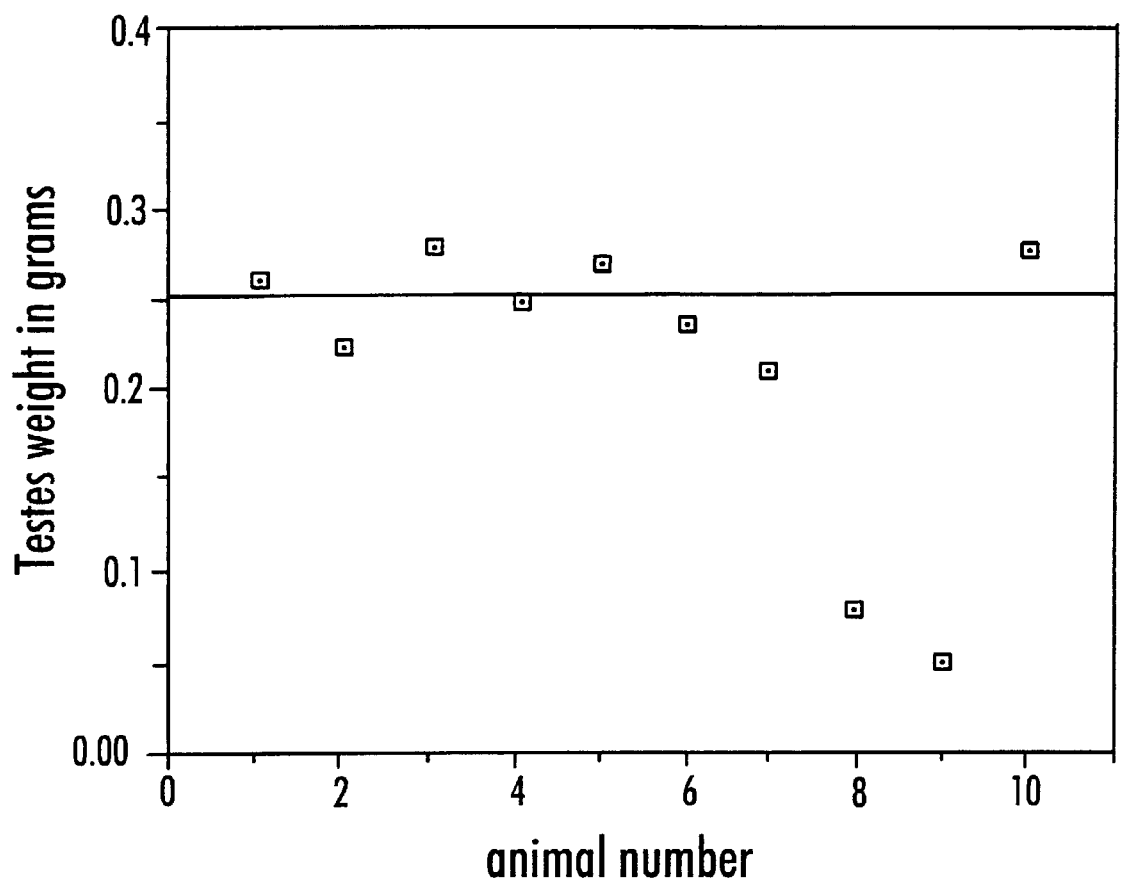
Figure 3:
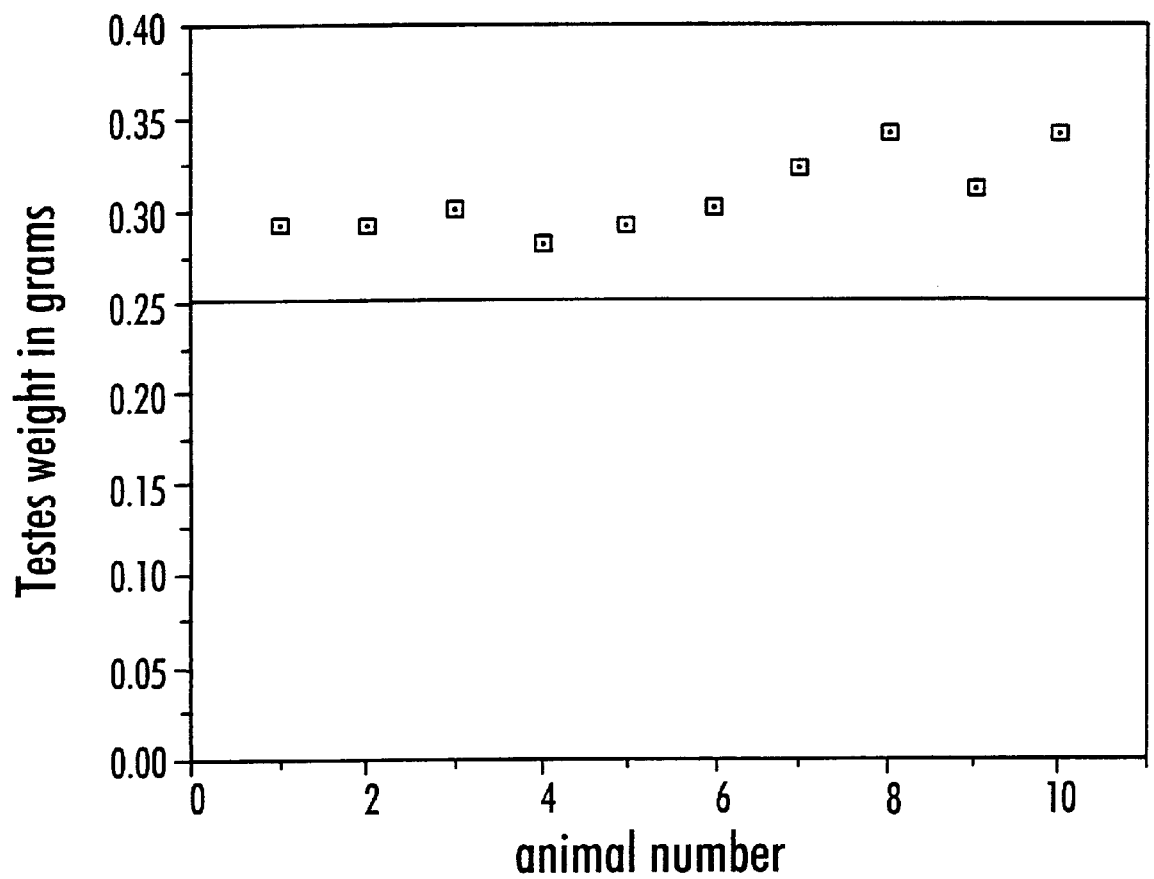
Figure 4:
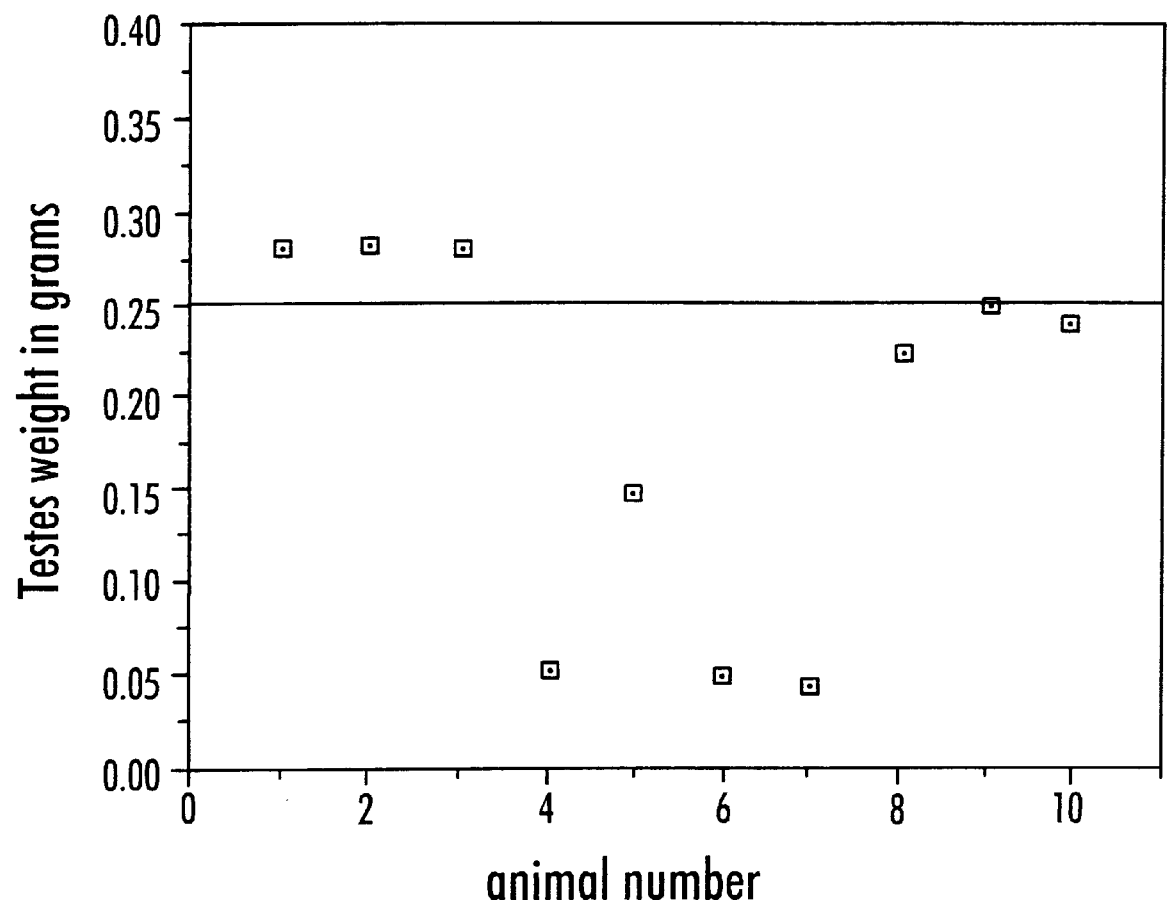
Figure 5:
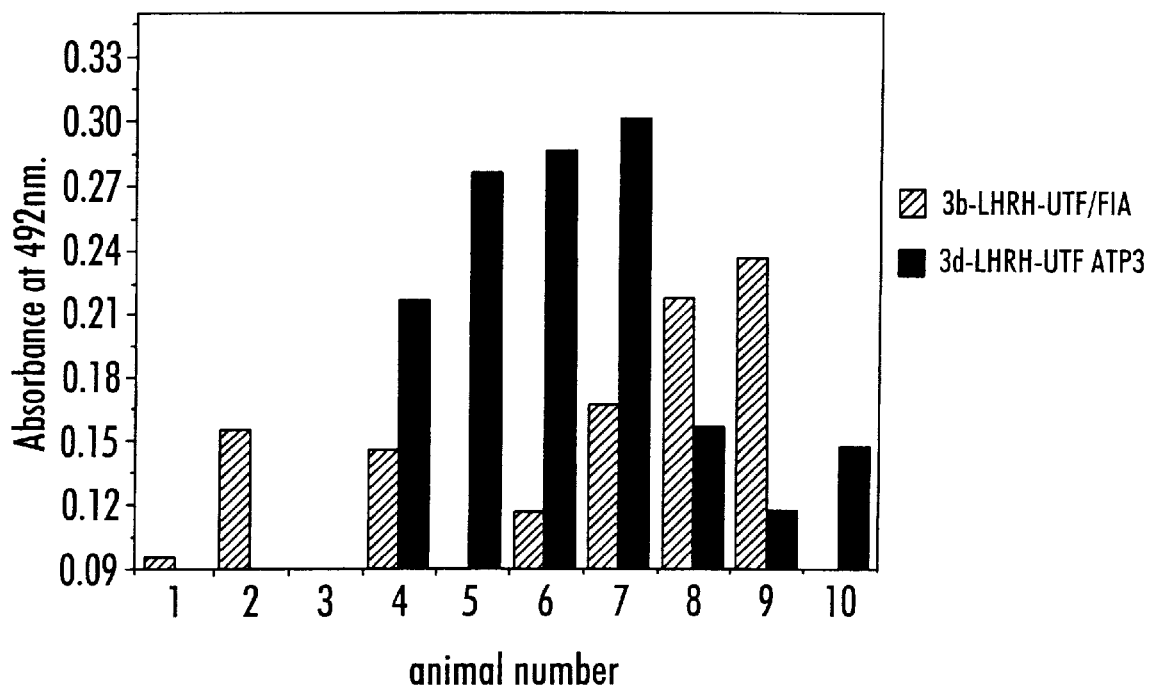
Figure 6A:
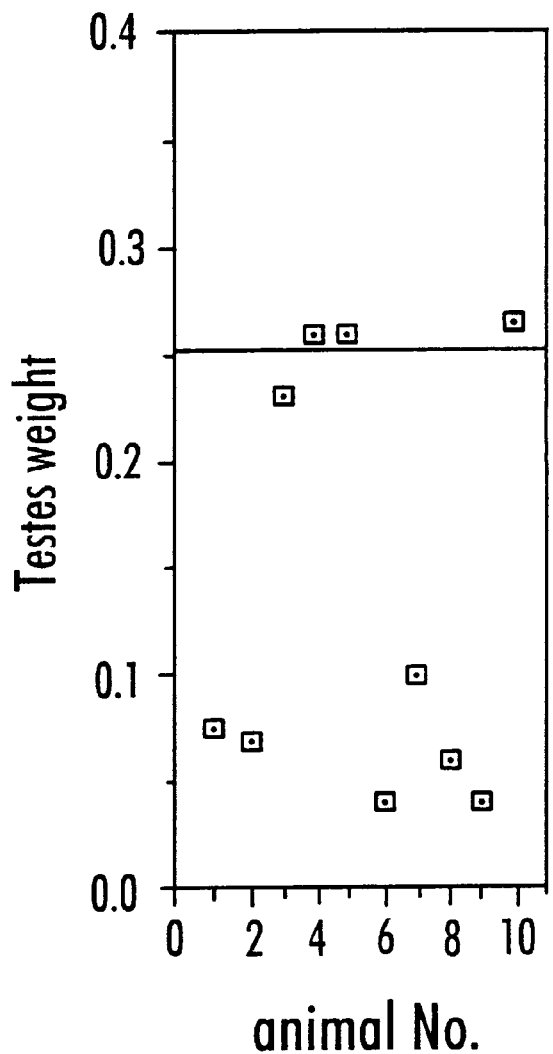
Figure 6B:
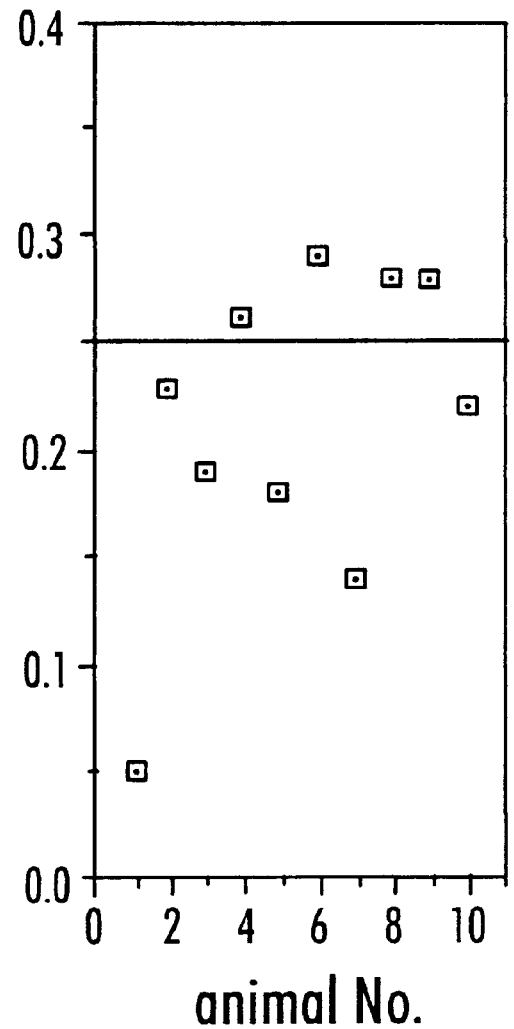
Figure 6C:
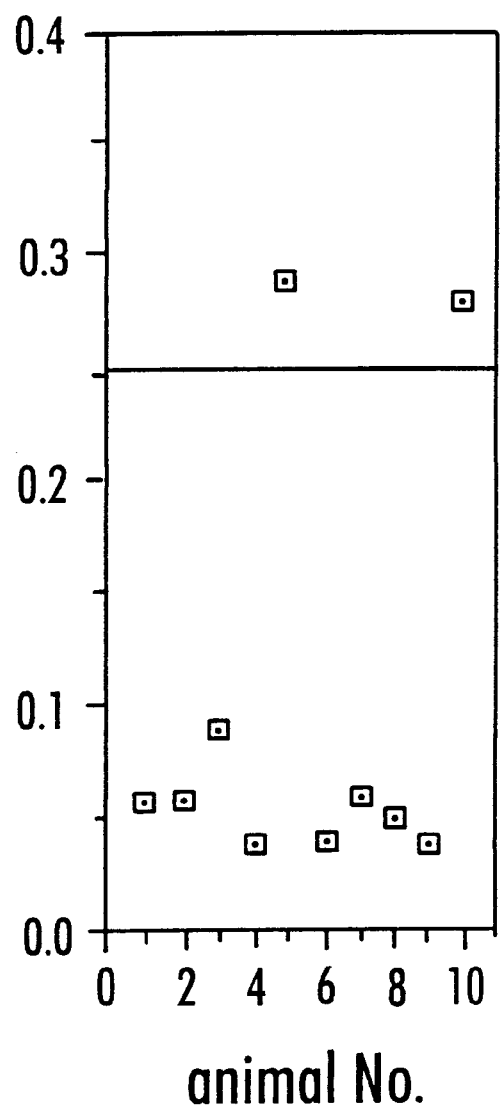
Figure 6D:
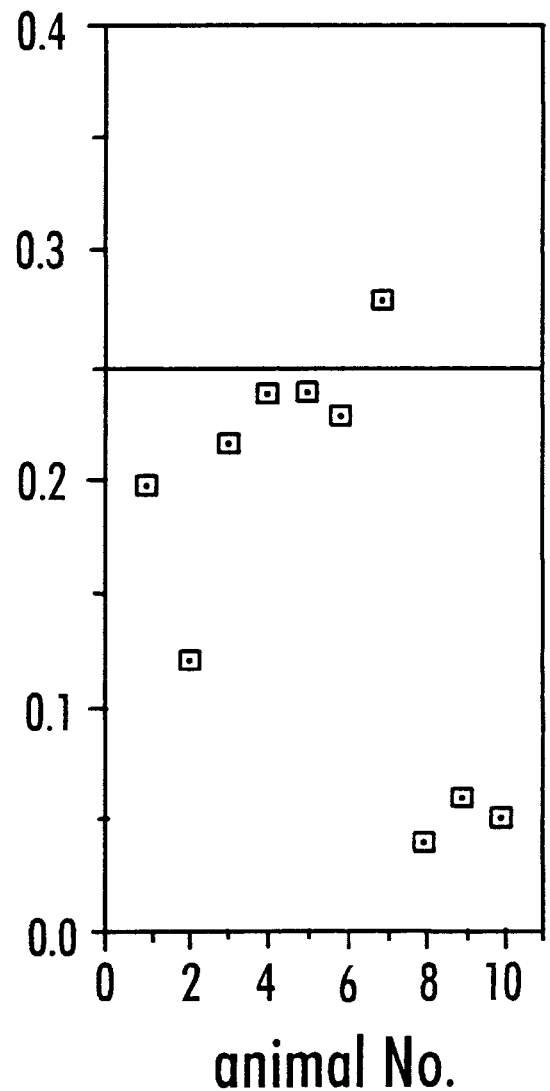
Figure 7:
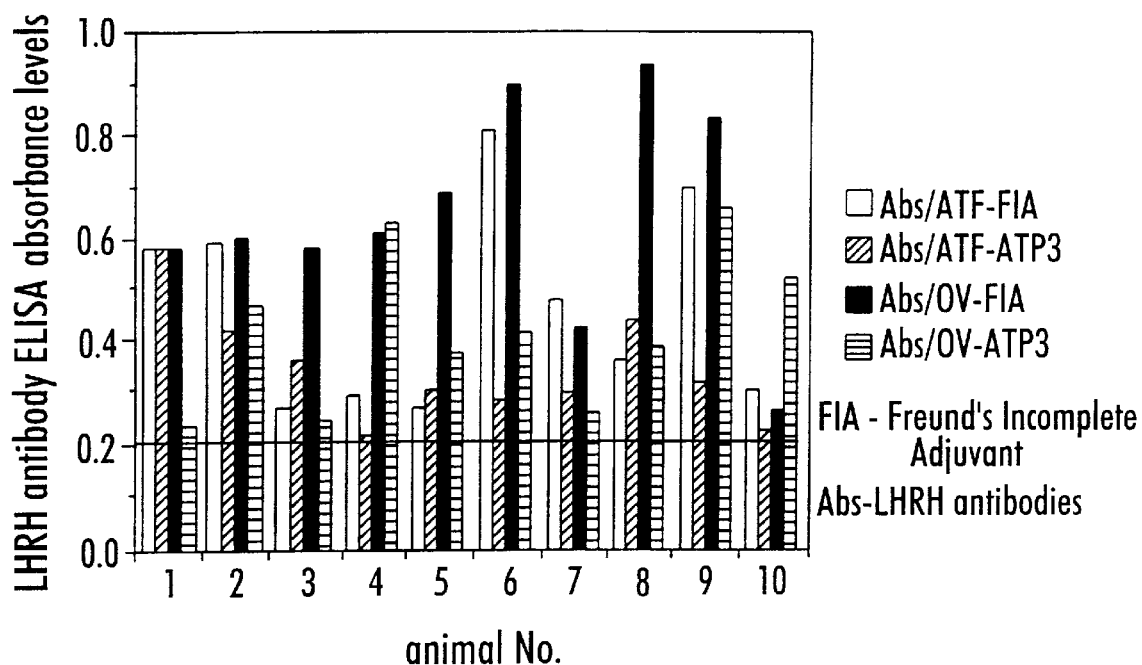
FIG. 7 shows the antibody results from the vaccinations set out in FIG. 6 □ATF-FIA; □ATF-ATP3; ■OV-FIA; and □OV-ATP3.

Oligoneuclotide directed mutagenesis and hybridisation screening was used to insert the LHRH related peptide into the pFEM/2 plasmid. DNA sequence analysis of a plasmid designated pMF2/1, isolated from one of these clones confirmed that the desired peptide had been grafted to the fimbrial subunit. pMF2/1 was used to transform *P. aeruginosa* K2 and expression of the modified subunit tested. A protein with a molecular weight greater than that of the unmodified fimbrial subunit was induced and could be detected extracellularly. The extracellular material was immunologically identified as *D. nodosus* fimbrial subunit and electron microscope examination revealed that the material existed as intact fimbriae. These results showed that fimbrial subunit bearing the LHRH graft was assembled and harvested as morphogenetically correct, extracellular structures.

Induction of Fimbrial Subunit Expression

For the induction of fimbriae in *P. aeruginosa,* colonies from 37° C. overnight culture plates were mixed into 8 ml portions of Tripticase Soy Broth (TSB) and 2 ml aliquots spread onto 245 mm×245 mm TSB agar plates containing 0.15 mg/ml of Carbenicillin. Plates were incubated at 42° C. for 18 to 24 hr and cells harvested by scraping into a minimal volume of phosphate-buffered saline. Fimbriae were precipitated from cell-free supernatents of the harvested cells in the presence of 0.1M magnesium chloride. Whole fimbrial samples were than analyzed for the protein content of samples using a dye-binding procedure BCA Pierce, USA) and samples taken for the electrophoretic analysis using a urea-SDS-polyacrylamide gel system.

Acid Treatment of PAK2 Fimbriae

Fimbrial preparations after $MgCl_2$ precipitation were washed with distilled water and resuspended at a concentration of 10 mg/ml. The pH of the fimbrial solution was adjusted to a pH of 1 using AR grade $H_3PO_4$ (85% w/v, Ajax Chemicals). The pH adjusted solution was then left undisturbed at 40° C. for 16 hours. The acid treated fimbriae were then neutralised with 100 $\mu$l of 10M NaOH and examined using non denaturing PAGE. The protein concentration was determined using a BCA method (Pierce, USA) and then stored at −20° C. until required.

Determination of LHRH antibody levels using ELISA.

Samples of blood were taken from mice at death and the sera from each stored at −20° C. until the antibody level was determined. A 200 $\mu$l aliquot of gelatin conjugated LHRH at 4° C. These were then washed twice with phosphate buffered saline containing 0.5 ml of Tween 20/liter (PBS-Tween) and blocked for 1.5 hours with 0.5 gms/100 ml gelatin. The plates were washed twice and 200 $\mu$l of 1:2500 mouse sera, from the experimental and control mice, added and left for 1.5 hours. These were again washed and a 1:2000 dilution of (horse radish peroxidase) HRP conjugated rabbit anti-mouse IgG (Dako Crop., Denmark) added to each. These were left for 1.5 hours washed 3 times with PBS-Tween and treated with OPD to determine the response. The absorbances were measured at 492 nm using a plate reader.

Immunization of Mice.

Twenty-five-day-old male Swiss/Balb c mice were immunized intraperitoneal (I.P.) with 100 $\mu$g to 150 $\mu$g of LHRH engineered PAK2 fimbriae in sterile distilled water at 1:1 (50 $\mu$l:50 $\mu$l) mixture with Freund's Incomplete Adjuvant (FIA) (Difco, UK) or Titremax (CytRx Crop, USA). A secondary immunisation was given at one month and the animals were sacrificed at two months after the primary immunisation. Blood and testes samples were taken at this point and used for LHRH antibody determination and statistical analysis.

Preparation of Ala-T Mono, Di and Tri Palmitate 1 miliequivalent of LHRH peptide was reacted with 3 miliequivalents of O(N-succinimidyl)-N,N,N',N'-tetramethyl uronium tetrafluoro borate (Fluka, 85975) in dimethyl formamide and N-ethyl-di-isopropyl amine was added to the apparent pH of 8.7. Active ester was formed in excess of 75% yield. To this solution 2 miliequivalents of ala-tris(palmitate, dipalmitate or tripalmitate) was added in dichloromethane (2–3 ml) and stirred for 1 hour. The apparent pH was readjusted to 8.5.

The reaction was monitored by HPLC using mobile phase consisting of (i) Buffer A—0.1% TFA: acetonitrile, 50:50, and (ii) Buffer B—acetonitrile: THF, 50:50 using a Novapak C4 column.

Purification of the products was by semi-preparative HPLC, on a C4 column and after the removal of solvents lypholised from t-butyl alcohol.

Results

In order to assess the effectiveness of the LHRH related peptide/fimbrial protein and peptide/fatty acid conjugates mice were immunised with a variety of vaccine combinations. FIGS. 1–4 shows a comparative vaccination trial using 10 animals per group. Mice were given two vaccinations at a four week interval and data collected four weeks after the second. The control animals (FIG. 1) and animals which received wild type fimbriae (fimbriae containing no peptide additions) (FIG. 3) showed no reduction in testes weight. (Testes weight of less than 0.25 g is considered a positive response) In contrast the animals vaccinated with acid treated LHRH related peptide/fimbrial protein with Freund's Incomplete Adjuvant (FIA) showed a marked reduction in testes weight. Similarly, mice receiving untreated LHRH related peptide/fimbrial protein in admixture with peptide/fatty acid conjugate showed a marked reduction in testes weight. FIG. 5 shows the antibody response in these animals.

FIG. 6 shows the results of mouse vaccinations with LHRH fimbrial protein conjugate and LHRH-ovalbumin conjugate with ATP3 fatty acid conjugate (ala-tris-tripalmitate). Groups of 10 mice were vaccine twice at four week intervals with combinations of the ATP3 conjugate and either LHRH conjugated to ovalbumin or LHRH conjugated to acid treated fimbriae. Data was collected four weeks after the second vaccination. The positive Control for the data set was LHRH acid treated fimbriae or LHRH-ovalbumin conjugate with FIA. Both LHRH presenting carrier molecules in combination with the fatty acid peptide conjugate yielded good physical responses, i.e., gonadal atrophy. The antibody responses for these animals are presented in FIG. 7.

Figure 8:
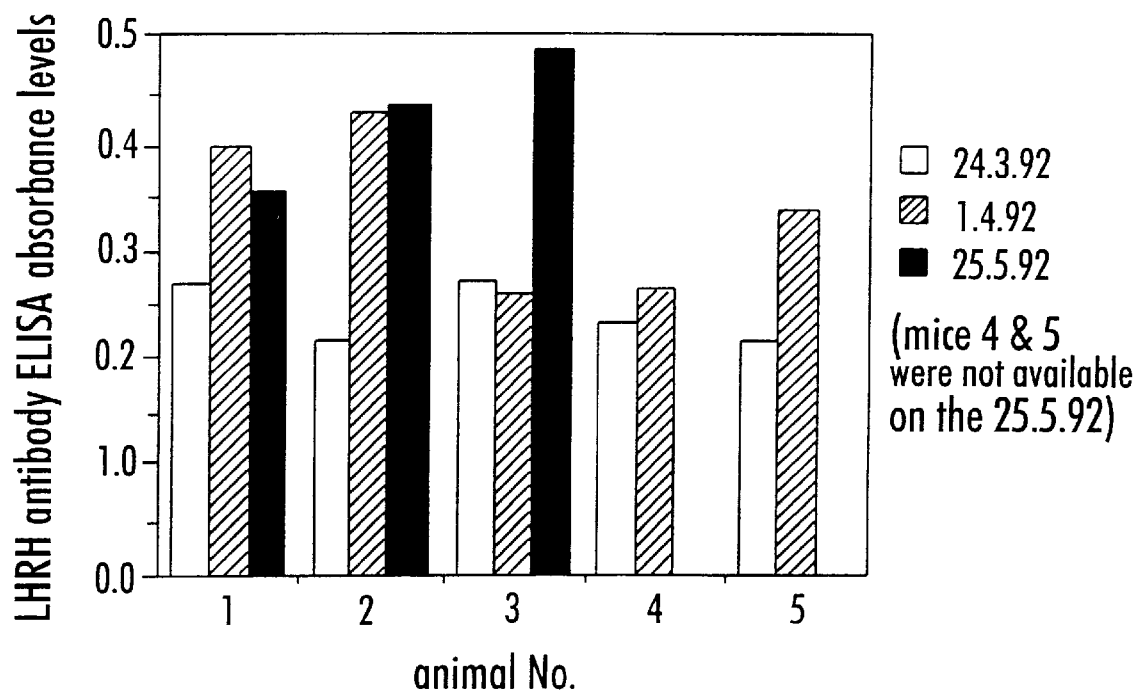
FIG. 8 shows antibody results obtained in immunocastrated mice after regeneration of testes were revaccinated with untreated LHRH-fimbriae and FIA; □prior to revaccination, □one week after revaccination, ■nine weeks after revaccination. The background absorbance level for this data was 0.19 units.

To exemplify the vaccines reversibility, five mice which had been vaccinated with LHRH-related peptide/fimbrial protein and (FIA) were left to recover after gonadal atrophy had occurred, i.e. 120 days after the primary vaccination. These mice were revaccinated with LHRH-fimbriae and 14 days later they were once again displaying marked gonadal atrophy. This indicates that the castration effect induced by the LHRH/fimbrial antigen is reversible and can be maintained with subsequent vaccinations. Antibody levels for these mice one week and four weeks after vaccination are presented in FIG. 8.

FIGS. 9 and 10 show that the antibody response and reduction is testes weight can be increased by using the immunopotentiating agents cimetidine and carnosine.

FIG. 11 shows that significant reductions in testes weight and increases in antibody levels can be obtained by administering acid treated LHRH-fimbriae conjugate in the absence of an adjuvanting agent. This ability to enhance antibody response using the Type 4 fimbriae is unexpected. It is believed that this unexpected result opens up the possibility of enhancing antibody responses by using Type 4 fimbriae as a "self-adjuvanting" carrier for peptides conjugated to the fimbriae.

FIG. 12 shows that significant reductions in testes weight and high antibody levels are obtained in animals vaccinated with acid treated LHRH-fimbriae in conjunction with LHRH-ATP3. It is of particular note that these reductions in testes weight and antibody levels were obtain without the use of oil or alum based adjuvants.

This "self-adjuvanting" ability of the vaccine admixture is of particular relevance given the inability to use oil based adjuvants in humans and the questions being raised concerning the use of alum based adjuvants.

As will be seen the present invention provides a vaccine which can be used to raise significant antibody levels against peptides without the use of oil or alum based adjuvants. This discovery is of great utility given the present concern regarding the use of oil and alum based adjuvants. Further, these findings open a new avenue for vaccines for human use.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A composition effective for raising antibodies to a peptide, the composition comprising a mixture comprising a peptide conjugated to 1 to 3 fatty acids, and the peptide conjugated to a carrier protein.

2. The composition as claimed in claim 1 in which the carrier protein is selected from the group consisting of fimbrial subunit protein, ovalbumin, bovine serum albumin, tetanus toxin and keyhole limpet haemocyanin.

3. The composition as claimed in claim 1 in which the carrier protein is a of mature fimbriae.

4. The composition as claimed in claim 3 in which the mature fimbriae is Type 4 fimbriae.

5. The composition as claimed in claim 1 in which the peptide is conjugated to 1 to 3 fatty acids via a tromethamine derivative or an ethanolamine derivative.

6. The composition as claimed in claim 3 in which the peptide/fimbrial protein conjugate is exposed to an acid treatment at pH less than or equal to 4.

7. The composition as claimed in claim 6 in which the peptide/fimbrial protein is exposed to an acid treatment at pH 1.

8. The composition as claimed in claim 1 in which the peptide is linked to 3 fatty acids each of which is the same fatty acid.

9. The composition as claimed in claim 1 which the fatty acid has a carbon chain of 3 to 18 carbon atoms.

10. The composition as claimed in claim 9 in which the fatty acid has a carbon chain of 16 carbon atoms.

11. The composition as claimed in claim 1 in which the composition further includes cimetidine, carnosine, cytokines or immunostimulatory peptides.

* * * * *